US00PP24199P2

(12) United States Plant Patent
Stemkens

(10) Patent No.: US PP24,199 P2
(45) Date of Patent: Jan. 28, 2014

(54) ***AUBRIETA* PLANT NAMED 'ABRZ0001'**

(50) Latin Name: *Aubrieta hybrida*
Varietal Denomination: ABRZ0001

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 94 days.

(21) Appl. No.: 13/507,175

(22) Filed: Jun. 11, 2012

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Joshua L. Price

(57) ABSTRACT

A new *Aubrieta* plant named 'ABRZ0001' particularly distinguished by the large velvety looking purple flowers, is early to flower and a compact and mounded plant habit that has good winter hardiness.

1 Drawing Sheet

Latin name of the genus and species of the plant claimed: *Aubrieta hybrida.*

Varietal denomination: 'ABRZ0001'.

BACKGROUND OF THE NEW PLANT

The present invention comprises a new *Aubrieta*, botanically known as *Aubrieta hybrida* and hereinafter referred to by the variety name 'ABRZ0001'.

'ABRZ0001' is a product of a planned breeding program. The new cultivar 'ABRZ0001' has large velvety looking purple flowers, is early to flower and a compact and mounded plant habit that has good winter hardiness.

'ABRZ0001' originates from a open-pollinated hybridization in a controlled breeding program in a greenhouse in Enkhuizen, The Netherlands in April 2007. The female parent was an unpatented, proprietary plant identified as 'K1616-52' with lighter colored flowers, bigger leaves and is more vigorous compared to 'ABRZ0001'.

The male parent of 'ABRZ0001' was unknown. The resultant seed was sown in a greenhouse in August 2007 in Enkhuizen, The Netherlands.

'ABRZ0001' was selected as one flowering plant within the progeny of the stated cross in March 2008 in a greenhouse in Enkhuizen, The Netherlands.

The first act of asexual reproduction of 'ABRZ0001' was accomplished when vegetative cuttings were taken from the initial selection in March 2008 in a greenhouse in Enkhuizen, The Netherlands.

BRIEF SUMMARY OF INVENTION

Horticultural examination of plants grown from cuttings of the plant initiated in March 2008 in Enkhuizen, The Netherlands, and continuing thereafter, has demonstrated that the combination of characteristics as herein disclosed for 'ABRZ0001' are firmly fixed and are retained through successive generations of asexual reproduction.

'ABRZ0001' has not been observed under all possible environmental conditions. The phenotype may vary significantly with variations in environment such as temperature, light intensity and day length.

A Plant Breeder's Right for this cultivar was applied for in Canada on Jun. 7, 2012, No. 12-7625. 'ABRZ0001' has not been made publicly available more than one year prior to the filing of this application.

The following traits have been repeatedly observed and are determined to be basic characteristics of the new variety. The combination of these characteristics distinguishes this *Aubrieta* as a new and distinct variety.

BRIEF DESCRIPTION OF THE PHOTOGRAPHS

The accompanying photographic drawings show typical flower and foliage characteristics of 'ABRZ0001' with colors being as true as possible with an illustration of this type.

Figure 1:
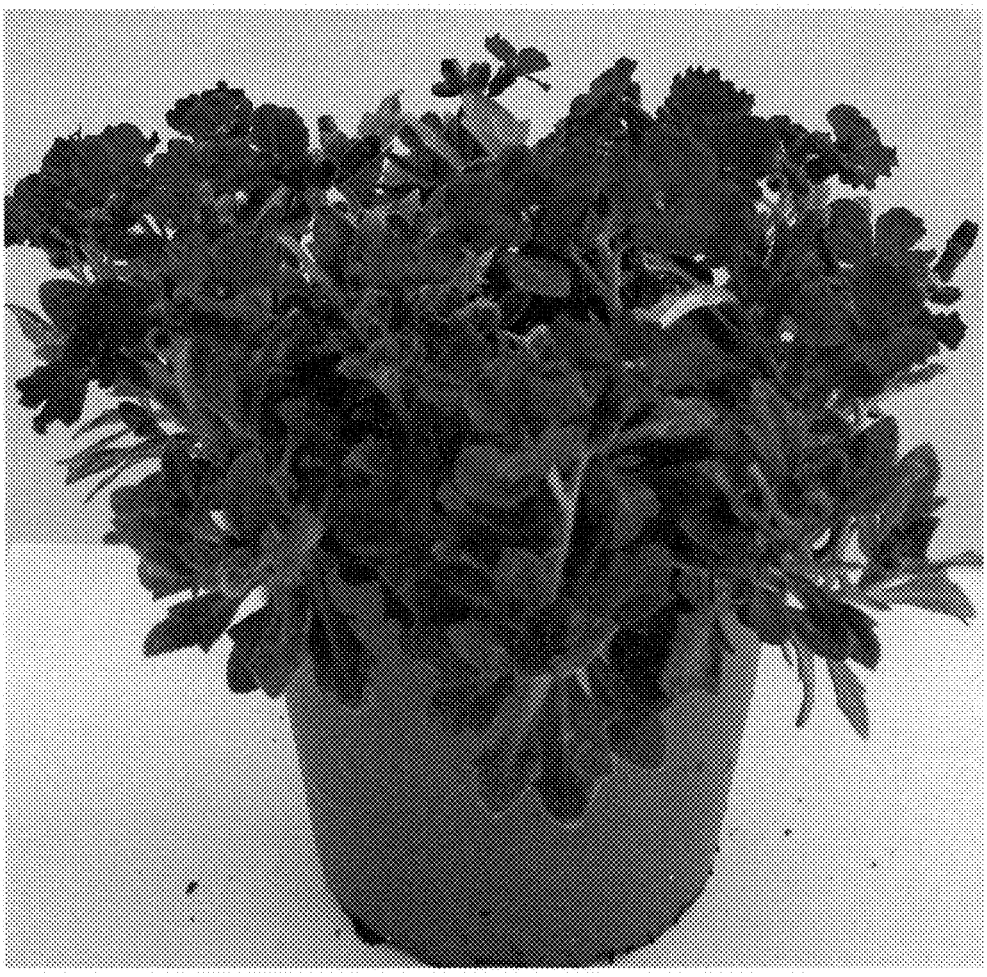
Figure 2:
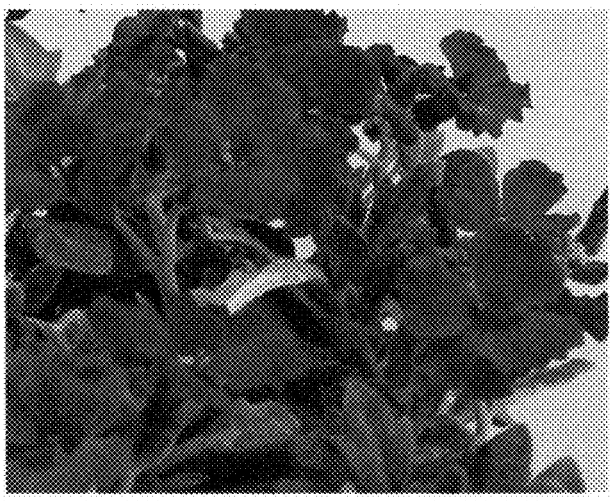

The photographic drawings show in FIG. 1 a flowering plant of the new variety and in FIG. 2 a close-up of the flowers.

DETAILED BOTANICAL DESCRIPTION

The plant descriptions and measurements were taken in Gilroy, Calif. under natural light in March 2012. These plants were approximately 22 week old and were growing in 1 gallon pots in shade-house trials. The plants used for the photographs were about 26 weeks old, growing in Enkhuizen, The Netherlands and the photographs were taken in March 2012.

Color Chart used: Royal Horticultural Society Colour Chart (R.H.S.) 2001

TABLE 1

DIFFERENCES BETWEEN THE NEW VARIETY 'ABRZ0001' AND A MOST SIMILAR VARIETY

| | 'ABRZ0001' | 'Aubnere' (U.S. Plant Pat. No. 21,841) |
|---|---|---|
| Flower color: | Darker | Lighter |
| Flower size: | Smaller | Larger |
| Plant habit: | Less vigorous | More vigorous |

Plant:
*Form, growth and habit.*—Compact, mounded, freely branching, and freely flowering.
*Plant height.*—8.0-9.0 cm.
*Plant height (inflorescence included)(cm).*—17.0-18.0 cm.
*Plant width.*—25.0-27.0 cm.

Roots:
*Number of days to initiate roots.*—About 6 days at about 18 degrees C.
*Number of days to produce a rooted cutting.*—2.5 weeks at 18 degrees C.
*Type.*—Fine, fibrous, free branching.
*Color.*—RHS N155B but whiter.

Foliage:
*Arrangement.*—Alternate.
*Immature, leaf color, upper surface.*—Closest to RHS 138A.
*Lower surface.*—Closest to RHS 138B.
*Mature, leaf color, upper surface.*—Closest to RHS 138A.
*Lower surface.*—Closest to RHS 138B.
*Length.*—1.7-2.0 cm.
*Width.*—0.9-1.1 cm.
*Shape.*—Ovate.
*Base shape.*—Attenuate.
*Apex shape.*—Mucronulate.
*Margin.*—Dentate.
*Texture.*—Stellate hairs.
*Color of veins, upper surface.*—About the same as foliage.
*Color of veins, lower surface.*—About the same as foliage.
*Pattern of veining.*—Pinnate.
*Petioles color.*—About RHS 138A.
*Petioles length.*—0.7-0.9 cm.
*Diameter of petiole.*—0.3 cm.
*Texture.*—Stellate hairs and hirsute on both sides.

Stem:
*Color of stem.*—RHS 144B to RHS 145D.
*Length of stem.*—6.0-9.0 cm.
*Diameter.*—0.3 cm.
*Length of internodes.*—0.4-0.6 cm.
*Texture.*—Stellate hairs and hirsute.
*Color of peduncle.*—Blotchy, between RHS 138A and RHS 138B.
*Length of peduncle.*—3.0-12.0 cm.
*Peduncle diameter.*—0.15 cm.
*Texture.*—Heavily covered with stellate hairs and hirsute.
*Color of pedicel.*—RHS 143C to RHS 138B.
*Length of pedicel.*—0.7-0.8 cm.
*Diameter of pedicel.*—0.075 cm.
*Texture.*—Stellate hairs and hirsute.

Inflorescence:
*Type.*—Single, cruciform, composed of 4 petals; flowers held above the plant.
*Quantity of inflorescences per plant.*—About 300.
*Lastingness of individual blooms on the plant.*—About 5 days.
*Fragrance.*—None.

Bud (just before opening/showing color):
*Color.*—Closest to RHS N79B.
*Length.*—1.1-1.4 cm.
*Width.*—0.3 cm.
*Shape.*—Oblong.

Corolla:
*Immature inflorescence: Diameter:* 1.4-1.5 cm. Color of petals, upper surface: Closest to RHS N79B. Lower surface: RHS N80A.
*Mature inflorescence.*—Flower diameter: 2.0-2.1 cm. Depth: 1.3-1.4 cm. Petal color, upper surface: Closest to RHS N79B. Lower surface: RHS N79C with lighter hue at the base. Length of petal: 1.7-1.8 cm. Width of petal: 0.5 cm at widest. Shape: Spathulate. Apex shape: Slightly retuse. Margin: Entire, and somewhat wavy. Petal texture, upper surface: Papillose. Lower surface: Papillose. Corolla tube color inside: RHS 157C. Tube color outside: Closest to RHS 159D. Corolla texture, inside: Papillose. Outside: Papillose.

Calyx:
*Quantity:* 4.
*Color, upper surface.*—RHS 137B overlaid basally with anthocyanins of closest to RHS 183C.
*Lower surface.*—RHS 137C.
*Length.*—0.7 cm.
*Width.*—0.2 cm.
*Shape.*—Oblong.
*Apex shape.*—Acute.
*Base.*—Fused.
*Margins.*—Entire.
*Texture, upper/inner surface.*—Smooth.
*Lower/outer surface.*—Stellate hairs.

Reproductive organs:
*Gynoecium.*—
*Pistil quantity.*—1.
*Length.*—0.8 cm.
*Style color.*—RHS 143C.
*Style length.*—0.3-0.4 cm.
*Stigma color.*—RHS 151D.
*Stigma shape.*—Disc-shaped.
*Ovary color.*—RHS 143D.
*Androecium.*—
*Stamens, quantity.*—6.
*Color of filaments.*—RHS 155B with a hint of RHS 71C terminally.
*Length filaments.*—0.6-0.9 cm.
*Anther color.*—RHS 10A.
*Anther length.*—0.1 cm.
*Anther shape.*—Ovate.
*Color of pollen.*—RHS 12C.
*Pollen amount.*—Moderate to normal.
*Fertility/seed set.*—Has not been determined to date.
*Disease/pest resistance.*—Has not been determined to date.

What is claimed is:

1. A new and distinct variety of *Aubrieta* plant named 'ABRZ0001' substantially as illustrated and described herein.

* * * * *